United States Patent [19]
Frederickson

[11] 4,430,327
[45] Feb. 7, 1984

[54] METHOD FOR TREATING PREGNANT FEMALES FOR PAIN AND ANXIETY

[75] Inventor: Robert C. A. Frederickson, Indianapolis, Ind.

[73] Assignee: Eli Lilly and Company, Indianapolis, Ind.

[21] Appl. No.: 379,539

[22] Filed: May 18, 1982

[51] Int. Cl.³ .............................................. A61K 37/02
[52] U.S. Cl. ................................................... 424/177
[58] Field of Search ................. 424/177; 260/112.5 R, 260/112.5 E

[56] References Cited

U.S. PATENT DOCUMENTS

| 4,148,785 | 4/1979 | Dheer et al. | 260/112.5 R |
| 4,178,371 | 12/1979 | Morgan | 260/112.5 R |
| 4,183,848 | 1/1980 | Garsky | 260/112.5 R |
| 4,259,234 | 3/1981 | Smithwick, Jr. et al. | 260/112.5 R |
| 4,322,342 | 3/1982 | Smithwick, Jr. et al. | 260/112.5 R |

Primary Examiner—Delbert R. Phillips
Assistant Examiner—F. T. Moezie
Attorney, Agent, or Firm—William C. Martens, Jr.; Arthur R. Whale

[57] ABSTRACT

A method is described for preventing or minimizing the effects of a drug on an embryo or a fetus by placental transport while alleviating pain and anxiety of the pregnant female by administering a pharmaceutically effective amount of a compound of the formula H-L-Tyr-D-Ala-Gly-L-Phe-L-(N-CH$_3$)Met-NH$_2$ or a pharmaceutically acceptable salt thereof.

8 Claims, No Drawings

METHOD FOR TREATING PREGNANT FEMALES FOR PAIN AND ANXIETY

BACKGROUND OF THE INVENTION

This invention is directed to a method for preventing or minimizing the effects of a drug on an embryo or a fetus by placental transport while alleviating pain and anxiety of the pregnant female during such pregnancy.

It has long been recognized that analgesics, at best, have limited use for women at all stages of pregnancy including labor and delivery. This limitation is due to the recognized transfer of the analgesic across the placental barrier with resultant potential detremental effect on the developing embryo or fetus. In addition, during labor, placental transport can produce depression of respiration of the newborn.

Thus, in the 1982 *Physician's Desk Reference*, 36th Edition, pp. 2025–2026, the following is stated with respect to meperidine:

> Meperidine should not be used in pregnant women prior to the labor period, unless in the judgment of the physician the potential benefits outweigh the possible hazards, because safe use in pregnancy prior to labor has not been established relative to possible adverse effects on fetal development.
>
> When used as an obstetrical analgesic, meperidine crosses the placental barrier and can produce depression of respiration and psychophysiologic functions in the newborn. Resuscitation may be required.

It has now been discovered that a particular pentapeptide having analgesic properties is highly advantageous in the treatment of pain and anxiety in pregnant women since it exhibits negligible, if any, transport across the placental barrier. The compound, metkephamid, has the structure

H-L-Tyr-D-Ala-Gly-L-Phe-L-(N-CH$_3$)Met-NH$_2$ and is covered by U.S. Pat. No. 4,322,342. It is to the use of this compound and pharmaceutically acceptable salts thereof that this invention is directed.

SUMMARY OF THE INVENTION

Thus, this invention is directed to a method for preventing or minimizing the effects of a drug on an embryo or a fetus by placental transport while alleviating pain and anxiety of the pregnant female during such pregnancy, which comprises administering to said pregnant female a pharmaceutically effective amount of a compound of the formula

H-L-Tyr-D-Ala-Gly-L-Phe-L-(N-CH$_3$)Met-NH$_2$ or a pharmaceutically acceptable salt thereof.

DETAILED DESCRIPTION OF THE INVENTION

As noted, this invention is directed to a method for preventing or minimizing the effects of a drug on an embryo or a fetus by placental transport while alleviating pain and anxiety of the pregnant female during such pregnancy. Although this action is available at anytime during the entire course of pregnancy, the dominating periods of use, of course, will be during the labor and delivery stages of the pregnancy, those stages having the highest incidence of pain and anxiety.

Metkephamid, the active compound of this invention, generally is administered in the form of its pharmaceutically acceptable non-toxic acid addition salt.

Pharmaceutically acceptable non-toxic acid addition salts include organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. The preferred non-toxic acid addition salt is that prepared from acetic acid. Any of these salts can be prepared by conventional methodology.

Metkephamid and non-toxic acid addition salts thereof can be used in a variety of pharmaceutical compositions and formulations and can be administered parenterally by a variety of conventional routes, such as intramuscular, intravenous, subcutaneous, and the like. Preferred routes are intramuscular or intravenous.

The pharmaceutical forms suitable for injection include sterile aqueous solutions or dispersions and sterile powders for reconstitution into sterile injectible solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating the compounds of this invention in the required amount of the appropriate solvent with various of the other ingredients, as desired.

Doses are administered to the pregnant female as necessary for pain and anxiety. Generally, the unit dose is from about 35 mg. to about 250 mg., and, preferably, from about 50 mg. to about 200 mg. Most preferably, metephamid is administered in an amount from about 75 mg. to about 150 mg.

The unexpected joining by metkephamid or its non-toxic acid addition salts of (1) significant analgesia and (2) little or no placental transfer make these compounds uniquely useful in treating pregnant females. This utility finds applicability at any point during pregnancy, including, in particular, the stages of labor of the mother and delivery of the fetus. Although applicable to any pregnant female, its most important application, of course, is to pregnant human females.

The analgesic properties of L-tyrosyl-D-alanyl-glycyl-L-phenylalanyl-N$^\alpha$-methyl-L-methionylamide acetate (metkephamide) is well documented in U.S. Pat. No. 4,322,342 as well as in numerous other publications (see, for example, S. S. Bloomfield, T. P. Barden, and J. Mitchell, *Clin. Pharmacol. Ther.* 31, 205 (1982); J. F. Calimlim, W. M. Wardell, C. Cox, L. Lasagna, and K. Sriwatanakul, *Clin. Pharmacol. Ther.* 31, 208–209 (1982)).

The examples following illustrate the extremely low levels of placental transport of metkephamid. These results are especially dramatic when viewed in the light of the high levels of placental transport obtained for meperidine, a recognized commercially available analgesic. The examples following are intended for illustrative purposes only and are not intended in any way to be limiting upon the scope of this invention.

Examples

Both pregnant ewes and pregnant female rats were examined for placental transport of metkephamid.

In the assay using pregnant ewes, fetal jugular veins and carotid arteries were catheterized and externalized. Maternal femoral arteries were also catheterized. Upon stabilization of the animals, metkephamid (acetate salt) was given intramuscularly, and maternal (10 ml.) and fetal (7 ml.) arterial blood were taken at 0, 10, 20, and 45 minutes. In this assay, 5 ewes at various stages of pregnancy ranging from day 115 to day 145 of a 145–147 day gestation period were used.

In the assay using rats, 19 female rats on day 20 of their gestation period were administered 50 mg./kg. body weight metkephamid (acetate salt) subcutaneously. Sixty minutes after administration, the rats were decapitated, and their blood was collected in glass tubes. The fetuses were removed from the uterus, and the blood was collected either after decapitation or via heart puncture using glass capillary tubes.

In assaying for metkephamid, 1 ml. serum samples containing 6.72 mg. NaF and 8.0 mg. ethylenediamine tetraacetic acid (EDTA) were prepared and precipitated by addition of 2 ml. acetone. The resulting supernatants were saturated with NaCl and extracted with ethyl acetate. The extracts were dried and derivatized with Fluram ® solution. The resulting solution was subjected to reverse phase high performance liquid chromatography and fluorescence detection.

For comparison, meperidine was administered to rats in the manner described for metkephamid. Meperidine content was assayed by adding 6.72 mg. NaF and 8.0 mg. EDTA to 1 ml. samples of serum. The samples were made alkaline with 0.1 ml. of 1.0 M NaOH and extracted with diethyl ether. The extracts were dried and dissolved in 0.3 ml. of ethyl acetate. An aliquot was injected into a gas chromatograph containing a 5 ft. glass column packed with 3% OV-1 on 100/120 mesh Gas Chrom Q. The oven temperature was 165° C., and the flame ionization detector temperature was 250° C.

The results from the foregoing are depicted in the Table following:

TABLE

| | | | Maternal and fetal serum levels (µg/ml) of metkephamid and meperidine at various times after administration to sheep (intramuscular) and rats (subcutaneous) | | | |
|---|---|---|---|---|---|---|
| | Dose | | Metkephamid | | Meperidine | |
| Species | mg/kg | Time (min) | Maternal | Fetal | Maternal | Fetal |
| Sheep | 5 | 0 | 0.0 | 0.0 | | |
| | 5 | 10 | 9.46 ± 3.01 | 0.0 | | |
| | 5 | 20 | 9.43 ± 2.6 | 0.0 | | |
| | 5 | 45 | 8.54 ± 2.6 | 0.0 | | |
| Rat | 50 | 60 | 7.17 ± 0.28 | 0.12 ± 0.04 | | |
| Rat | 50 | 45 | | | 3.73 ± 0.89 | 2.02 ± 0.23 |

From the above it is noted that, for sheep, the maternal serum levels of metkephamid after a dose of 5 mg./kg. were 8–10 µg./ml. at 10, 20, and 45 minutes after injection whereas fetal levels were undetectable at all measured times. The limit of sensitivity of the assay is about 50 ng./ml.; therefore, the ratio of fetal:maternal levels is <1:200. In rat, the fetal:maternal ratio at 60 minutes (time of peak blood levels) after subcutaneous administration of 50 mg./kg. metkephamid was about 1:60. By contrast, the fetal:maternal ratio for meperidine was about 1:1.8.

I claim:

1. A method for preventing or minimizing the effects of a drug on an embryo or a fetus by placental transport while alleviating pain and anxiety of the pregnant female during such pregnancy, which comprises administering to said pregnant female a pharmaceutically effective amount of a compound of the formula H-L-Tyr-D-Ala-Gly-L-Phe-L-(N-CH₃)Met-NH₂ or a pharmaceutically acceptable salt thereof.

2. Method of claim 1, in which said pregnant female is a pregnant human female.

3. Method of claim 2, in which the compound is administered as its acetate salt.

4. Method of claim 2, in which the compound is administered intravenously.

5. Method of claim 2, in which the compound is administered intramuscularly.

6. Method of claim 2, in which the compound is administered in a unit dose of from about 35 mg. to about 250 mg.

7. Method of claim 6, in which the compound is administered in a unit dose of from about 50 mg. to about 200 mg.

8. Method of claim 7, in which the compound is administered in a unit dose of from about 75 mg. to about 150 mg.

* * * * *